(12) United States Patent
Cox et al.

(10) Patent No.: US 11,937,838 B2
(45) Date of Patent: Mar. 26, 2024

(54) METHODS AND APPARATUS FOR TREATING EMBOLISM

(71) Applicant: Inari Medical, Inc., Irvine, CA (US)

(72) Inventors: Brian J. Cox, Laguna Niguel, CA (US); Paul Lubock, Laguna Niguel/Monarch Beach, CA (US); Robert Rosenbluth, Laguna Niguel, CA (US); Richard Quick, Mission Viejo, CA (US); Philippe Marchand, Lake Forest, CA (US)

(73) Assignee: Inari Medical, Inc., Irvine, CA (US)

( * ) Notice: Subject to any disclaimer, the term of this patent is extended or adjusted under 35 U.S.C. 154(b) by 3 days.

(21) Appl. No.: 17/357,817

(22) Filed: Jun. 24, 2021

(65) Prior Publication Data
US 2022/0022898 A1    Jan. 27, 2022

Related U.S. Application Data

(63) Continuation of application No. 16/224,193, filed on Dec. 18, 2018, now Pat. No. 11,058,445, which is a
(Continued)

(51) Int. Cl.
*A61B 17/221* (2006.01)
*A61B 17/22* (2006.01)
(Continued)

(52) U.S. Cl.
CPC ............ *A61B 17/221* (2013.01); *A61B 17/22* (2013.01); *A61M 25/0074* (2013.01);
(Continued)

(58) Field of Classification Search
CPC .... A61B 2017/2212; A61B 2017/2215; A61B 2017/2217; A61B 17/22; A61B 17/221;
(Continued)

(56) References Cited

U.S. PATENT DOCUMENTS

| 1,101,890 A | 6/1914 | Tunstead |
| 2,784,717 A | 3/1957 | Thompson |

(Continued)

FOREIGN PATENT DOCUMENTS

| AU | 2015210338 | 8/2015 |
| CN | 102186427 | 9/2011 |

(Continued)

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993 6 pgs.

(Continued)

*Primary Examiner* — Tuan V Nguyen
(74) *Attorney, Agent, or Firm* — Perkins Coie LLP

(57) ABSTRACT

A device and method for intravascular treatment of an embolism, and particularly a pulmonary embolism, is disclosed herein. One aspect of the present technology, for example, is directed toward a clot treatment device that includes a support member having a plurality of first clot engagement members and second clot engagement members positioned about the circumference of a distal portion of the support member. In an undeployed state, individual first clot engagement members can be linear and have a first length, and individual second clot engagement members can be linear and have a second length that is less than the first length. The clot engagement members can be configured to penetrate clot material along an arcuate path and hold clot material to the clot treatment device.

16 Claims, 10 Drawing Sheets

Related U.S. Application Data continuation of application No. 15/031,102, filed as application No. PCT/US2014/061645 on Oct. 21, 2014, now Pat. No. 10,238,406, which is a continuation-in-part of application No. 14/299,933, filed on Jun. 9, 2014, now Pat. No. 9,259,237, which is a continuation-in-part of application No. 14/299,997, filed on Jun. 9, 2014, now abandoned.

(60) Provisional application No. 61/949,953, filed on Mar. 7, 2014, provisional application No. 61/893,859, filed on Oct. 21, 2013.

(51) Int. Cl.
| | | |
|---|---|---|
| A61M 25/00 | (2006.01) | |
| A61M 25/01 | (2006.01) | |
| A61M 25/06 | (2006.01) | |
| A61M 25/10 | (2013.01) | |
| A61B 17/32 | (2006.01) | |

(52) U.S. Cl.
CPC ........ *A61M 25/01* (2013.01); *A61M 25/0662* (2013.01); *A61M 25/10* (2013.01); *A61B 2017/22034* (2013.01); *A61B 2017/22067* (2013.01); *A61B 2017/22068* (2013.01); *A61B 2017/320064* (2013.01); *A61M 2025/1004* (2013.01); *A61M 2025/1047* (2013.01)

(58) Field of Classification Search
CPC ....... A61B 17/22012; A61B 17/22031; A61M 25/0074; A61M 25/01; A61M 25/0662; A61M 25/10

See application file for complete search history.

(56) References Cited

U.S. PATENT DOCUMENTS

| | | |
|---|---|---|
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,675,657 A | 7/1972 | Gauthier |
| 3,785,380 A | 1/1974 | Brumfield |
| 3,860,006 A | 1/1975 | Patel |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,776,337 A | 10/1988 | Palmaz |
| 4,790,812 A | 12/1988 | Hawkins, Jr. et al. |
| 4,863,440 A | 9/1989 | Chin et al. |
| 4,870,953 A | 10/1989 | DonMichael et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,234,403 A | 8/1993 | Yoda et al. |
| 5,242,461 A | 9/1993 | Kortenbach et al. |
| 5,244,619 A | 9/1993 | Burnham |
| 5,329,923 A | 7/1994 | Lundquist |
| 5,360,417 A | 11/1994 | Gravener et al. |
| 5,364,345 A | 11/1994 | Lowery et al. |
| 5,376,101 A | 12/1994 | Green et al. |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,876,414 A | 3/1999 | Straub |
| 5,895,406 A | 4/1999 | Gray et al. |
| 5,908,435 A * | 6/1999 | Samuels .......... A61B 17/22032 606/127 |
| 5,911,710 A | 6/1999 | Barry et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,946 A | 11/2000 | Broome et al. |

(56) References Cited

U.S. PATENT DOCUMENTS

| | | |
|---|---|---|
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,569,181 B1 | 5/2003 | Burns |
| 6,575,995 B1 | 6/2003 | Huter et al. |
| 6,589,263 B1 | 7/2003 | Hopkins et al. |
| 6,589,264 B1 | 7/2003 | Barbut et al. |
| 6,596,011 B2 | 7/2003 | Johnson et al. |
| 6,602,271 B2 | 8/2003 | Adams et al. |
| 6,605,074 B2 | 8/2003 | Zadno-Azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-Azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 | 6/2005 | Hajianpour |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 | 5/2007 | Hogendijk |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 | 11/2010 | Nieoson et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |

(56) References Cited

U.S. PATENT DOCUMENTS

| | | |
|---|---|---|
| 8,523,897 B2 | 9/2013 | van der Burg et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,771,289 B2 | 7/2014 | Mohluddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | Van der Burg et al. |
| 9,173,668 B2 | 11/2015 | Ulm, III |
| 9,186,487 B2 | 11/2015 | Dubrul et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,526,864 B2 | 12/2016 | Quick |
| 9,526,865 B2 | 12/2016 | Quick |
| 9,532,792 B2 | 1/2017 | Galdonik et al. |
| 9,566,073 B2 | 2/2017 | Kassab et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Kroilk et al. |
| 9,827,084 B2 | 11/2017 | Bonnette et al. |
| 9,844,386 B2 | 12/2017 | Nguyen et al. |
| 9,844,387 B2 | 12/2017 | Marchand et al. |
| 9,848,975 B2 | 12/2017 | Hauser |
| 9,849,014 B2 | 12/2017 | Kusleika |
| 9,884,387 B2 | 2/2018 | Plha |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,183,159 B2 | 1/2019 | Nobles et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,384,034 B2 | 8/2019 | Carrison et al. |
| 10,456,555 B2 | 10/2019 | Carrison et al. |
| 10,478,535 B2 | 11/2019 | Ogle |
| 10,485,952 B2 | 11/2019 | Carrison et al. |
| 10,524,811 B2 | 1/2020 | Marchand et al. |
| 10,531,883 B1 | 1/2020 | Deville et al. |
| 10,588,655 B2 | 3/2020 | Rosenbluth et al. |
| 10,648,268 B2 | 5/2020 | Jaffrey et al. |
| 10,695,159 B2 | 6/2020 | Hauser |
| 10,709,471 B2 | 7/2020 | Rosenbluth et al. |
| 10,772,636 B2 | 9/2020 | Kassab et al. |
| 10,799,331 B2 | 10/2020 | Hauser |
| 10,912,577 B2 | 2/2021 | Marchand et al. |
| 10,926,060 B2 | 2/2021 | Stern et al. |
| 10,953,195 B2 | 3/2021 | Jalgaonkar et al. |
| 10,960,114 B2 | 3/2021 | Goisis |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,147,571 B2 | 10/2021 | Cox et al. |
| 11,154,314 B2 | 10/2021 | Quick |
| 11,166,703 B2 | 11/2021 | Kassab et al. |
| 11,185,664 B2 | 11/2021 | Carrison et al. |
| 11,224,450 B2 | 1/2022 | Chou et al. |
| 11,224,721 B2 | 1/2022 | Carrison et al. |
| 11,259,821 B2 | 3/2022 | Buck et al. |
| 11,305,094 B2 | 4/2022 | Carrison et al. |
| 11,383,064 B2 | 7/2022 | Carrison et al. |
| 11,395,903 B2 | 7/2022 | Carrison et al. |
| 11,406,801 B2 | 8/2022 | Fojtik et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,529,158 B2 | 12/2022 | Hauser |
| 11,554,005 B2 | 1/2023 | Merritt et al. |
| 11,559,382 B2 | 1/2023 | Merritt et al. |
| 11,576,691 B2 | 2/2023 | Chou et al. |
| 11,596,768 B2 | 3/2023 | Stern et al. |
| 11,642,209 B2 | 5/2023 | Merritt et al. |
| 11,648,028 B2 | 5/2023 | Rosenbluth et al. |
| 11,697,011 B2 | 7/2023 | Merritt et al. |
| 11,697,012 B2 | 7/2023 | Merritt et al. |
| 11,744,691 B2 | 9/2023 | Merritt et al. |

(56) References Cited

U.S. PATENT DOCUMENTS

| | | |
|---|---|---|
| 11,806,033 B2 | 11/2023 | Marchand et al. |
| 11,832,837 B2 | 12/2023 | Hauser |
| 11,832,838 B2 | 12/2023 | Hauser |
| 11,833,023 B2 | 12/2023 | Hauser |
| 11,839,393 B2 | 12/2023 | Hauser |
| 11,844,921 B2 | 12/2023 | Merritt et al. |
| 11,849,963 B2 | 12/2023 | Quick |
| 2001/0004699 A1 | 6/2001 | Gittings et al. |
| 2001/0031981 A1 | 10/2001 | Evans et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0023263 A1 | 1/2003 | Krolik et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191516 A1 | 10/2003 | Weldon et al. |
| 2003/0208224 A1 | 11/2003 | Broome |
| 2003/0216774 A1 | 11/2003 | Larson |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0089533 A1 | 4/2006 | Ziegler et al. |
| 2006/0100662 A1 | 5/2006 | Daniel et al. |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai et al. |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |

(56) References Cited

U.S. PATENT DOCUMENTS

| | | |
|---|---|---|
| 2010/0318178 A1 | 12/2010 | Rapaport et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jernison |
| 2014/0257363 A1 | 9/2014 | Lippert |
| 2014/0276403 A1 | 9/2014 | Follmer et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth et al. |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth |
| 2015/0305859 A1 | 10/2015 | Eller |
| 2015/0352325 A1 | 12/2015 | Quick |
| 2015/0360001 A1 | 12/2015 | Quick |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0135829 A1 | 5/2016 | Holoehwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0262774 A1 | 9/2016 | Honda |

(56) References Cited

U.S. PATENT DOCUMENTS

| | | |
|---|---|---|
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0172591 A1 | 6/2017 | Ulm, III |
| 2017/0112513 A1 | 7/2017 | Marchand et al. |
| 2017/0189041 A1 | 7/2017 | Cox et al. |
| 2017/0196576 A1 | 7/2017 | Long et al. |
| 2017/0233908 A1 | 8/2017 | Kroczynski et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0296240 A1 | 10/2018 | Rosenbluth et al. |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2020/0022711 A1 | 1/2020 | Look et al. |
| 2020/0046368 A1 | 2/2020 | Merritt et al. |
| 2020/0046940 A1 | 2/2020 | Carrison et al. |
| 2020/0113412 A1 | 4/2020 | Jensen |
| 2020/0121334 A1 | 4/2020 | Galdonik et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0128182 A1 | 5/2021 | Teigen et al. |
| 2021/0137667 A1 | 5/2021 | Sonnette et al. |
| 2021/0138194 A1 | 5/2021 | Carrison et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0033888 A1 | 2/2022 | Schnall-Levin et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0240959 A1 | 8/2022 | Quick |
| 2022/0346800 A1 | 11/2022 | Merritt et al. |
| 2022/0346801 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2023/0046775 A1 | 2/2023 | Quick |
| 2023/0059721 A1 | 2/2023 | Chou et al. |
| 2023/0062809 A1 | 3/2023 | Merritt et al. |
| 2023/0070120 A1 | 3/2023 | Cox et al. |
| 2023/0122587 A1 | 4/2023 | Chou et al. |
| 2023/0200970 A1 | 6/2023 | Merritt et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |

FOREIGN PATENT DOCUMENTS

| | | |
|---|---|---|
| CN | 103764049 | 4/2014 |
| CN | 103932756 | 7/2014 |
| CN | 104068910 | 10/2014 |
| CN | 106178227 | 12/2016 |

(56) References Cited

FOREIGN PATENT DOCUMENTS

| | | |
|---|---|---|
| CN | 108348319 | 7/2018 |
| CN | 110652645 | 1/2020 |
| CN | 111281482 | 6/2020 |
| DE | 102017004383 | 7/2018 |
| EP | 1254634 | 11/2002 |
| EP | 1867290 | 2/2013 |
| EP | 2942624 | 11/2015 |
| EP | 3583972 | 12/2019 |
| EP | 3589348 | 1/2020 |
| EP | 3620204 | 3/2020 |
| EP | 3013404 | 4/2020 |
| EP | 4137070 | 2/2023 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2004097807 | 4/2004 |
| JP | 2005-095242 | 6/2005 |
| JP | 2005230132 | 9/2005 |
| JP | 2005323702 | 11/2005 |
| JP | 2006094876 | 4/2006 |
| JP | 2011526820 | 1/2010 |
| WO | WO1997017889 | 5/1997 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO0032118 | 6/2000 |
| WO | WO2000053120 | 9/2000 |
| WO | WO0202162 | 1/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2017024258 | 2/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |

OTHER PUBLICATIONS

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, dated Jan. 17, 2014, 7 pages.

International Search Report and Written Opinion for International App. No. PCT/US2014/046567, dated Nov. 3, 2014, 13 pages.

International Search Report and Written Opinion for International App. No. PCT/US2014/061645, dated Jan. 23, 2015, 15 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of Chest Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al., "Massive pulmonary embolism: review of management strategies with a focus on catheter-based techniques", Expert Rev. Cardiovasc. Ther. 8(6), 863-873 (2010).

Liu, S. et al., "Massive Pulmonary Embolism: Treatment with the Rotarex Thrombectomy System", Cardiovascular Interventional Radiology; 2011: 34:106-113.

(56) References Cited

OTHER PUBLICATIONS

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "Adapt Fast study: a direct aspiration first pass technique for acute stroke thrombectomy." J Neurointervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2015/034987 filed Jun. 9, 2015, Applicant: Inceptus Medical, LLC, dated Sep. 17, 2015, 12 pages.
International Search Report and Written Opinion for International App. No. PCT/US2016/067628 filed Dec. 19, 2016, Applicant: Inari Medical, Inc., dated Apr. 10, 2017, 11 pages.
Goldhaber, S. et al. "Percutaneous Mechanical Thrombectomy for Acute Pulmonary Embolism—a Double-Edged Sword," American College of Chest Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., dated Sep. 15, 2017, 19 pages.
International Search Report and Written Opinion for International App. No. PCT/US2016/058536, Date of Filing: Oct. 24, 2016, Applicant: Inari Medical, Inc., dated Mar. 13, 2017, 14 pages.
International Search Report and Written Opinion for International App. No. PCT/US2018/048786, Date of Filing: Aug. 30, 2018, Applicant: Inari Medical, Inc., dated Dec. 13, 2018, 12 pages.
International Search Report and Written Opinion for International App. No. PCT/US2018/055780, Date of Filing: Oct. 13, 2018, Applicant: Inceptus Medical LLC., dated Jan. 22, 2019, 8 pages.
International Search Report and Written Opinion for International App, No. PCT/US2019/045794, Date of Filing: Aug. 8, 2019, Applicant: Inari Medical, Inc., dated Nov. 1, 2019, 17 pages.
International Search Report and Written Opinion for International App. No. PCT/US2020/056067, Date of Filing: Oct. 16, 2020; Applicant: Inari Medical, Inc., dated Jan. 22, 2021, 8 pages.
International Search Report and Written Opinion for International App. No. PCT/US2020/055645, Date of Filing: Dec. 17. 2020; Applicant: Inari Medical, Inc., dated Apr. 14, 2021, 12 pages.
Vorwerk, D. MD, et al., "Use of a Temporary Caval Filter to Assist Percutaneous Iliocaval Thrombectomy: Experimental Results." SCVIR, 1995, 4 pages.
Wikipedia; Embolectomy; retrieved from the internet: https://en.wikipedia.org/wiki/Embolectorny; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
Youtube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the Internet: http://www.ev3.net/neuro/intl/remodeling-devices/solitaire-ab.htm; © 2015; 2 pgs.; retrieved/printed: Mar. 24, 2016.
International Search Report and Written Opinion for International App. No. PCT/US21/35965, Date of Filing: Jun. 4, 2021, Applicant: Inari Medical, Inc., dated Sep. 28, 2021, 12 pages.
International Search Report and Written Opinion for International App. No. PCT/US21/45072 Date of Filing: Aug. 6, 2021, Applicant: Inari Medical, Inc., dated Jan. 20, 2022, 10 pages.
International Search Report and Written Opinion for International App. No. PCT/US21/58793; Date of Filing: Nov. 10, 2021, Applicant: Inari Medical, Inc., dated Mar. 16, 2022, 13 pages.
International Search Report and Written Opinion for International App. No. PCT/US21/59718; Date of Filing: Nov. 17, 2021, Applicant: Inari Medical, Inc., dated Mar. 22, 2022, 13 pages.
International Search Report and Written Opinion for International App. No. PCT/US21/59735; Date of Filing: Nov. 17, 2021, Applicant: Inari Medical, Inc., dated Mar. 22, 2022, 11 pages.
International Search Report and Written Opinion for International App. No. PCT/US23/60502; filed Jan. 11, 2023, Applicant: Inari Medical, Inc., dated May 25, 2023, 9 pages.
International Search Report and Written Opinion for International App. No. PCT/US23/61256; filed Jan. 25, 2023, Applicant: Inari Medical, Inc., dated Jun. 7, 2023, 8 pages.
Gross et al., "Dump the pump: manual aspiration thrombectomy (MAT) with a syringe is technically effective, expeditious, and cost-efficient," J NeuroIntervent Surg, 2018, 4 pages.
International Search Report and Written Opinion for International App. No. PCT/US23/66538; filed May 3, 2023, Applicant: Inari Medical, Inc., dated Jan. 4, 2024, 14 pages.
International Search Report and Written Opinion for International App. No. PCT/US23/60927; filed Jan. 19, 2023, Applicant: Inari Medical, Inc., dated Jul. 20, 2023, 12 pages.
Extended European Search Report issued for EP Application No. 20877370.5, dated Oct. 17, 2023, 11 pages.

(56) References Cited

OTHER PUBLICATIONS

International Search Report and Written Opinion for International App. No. PCT/US23/65128; filed Mar. 30, 2023, Applicant: Inari Medical, Inc., dated Nov. 14, 2023, 14 pages.

* cited by examiner

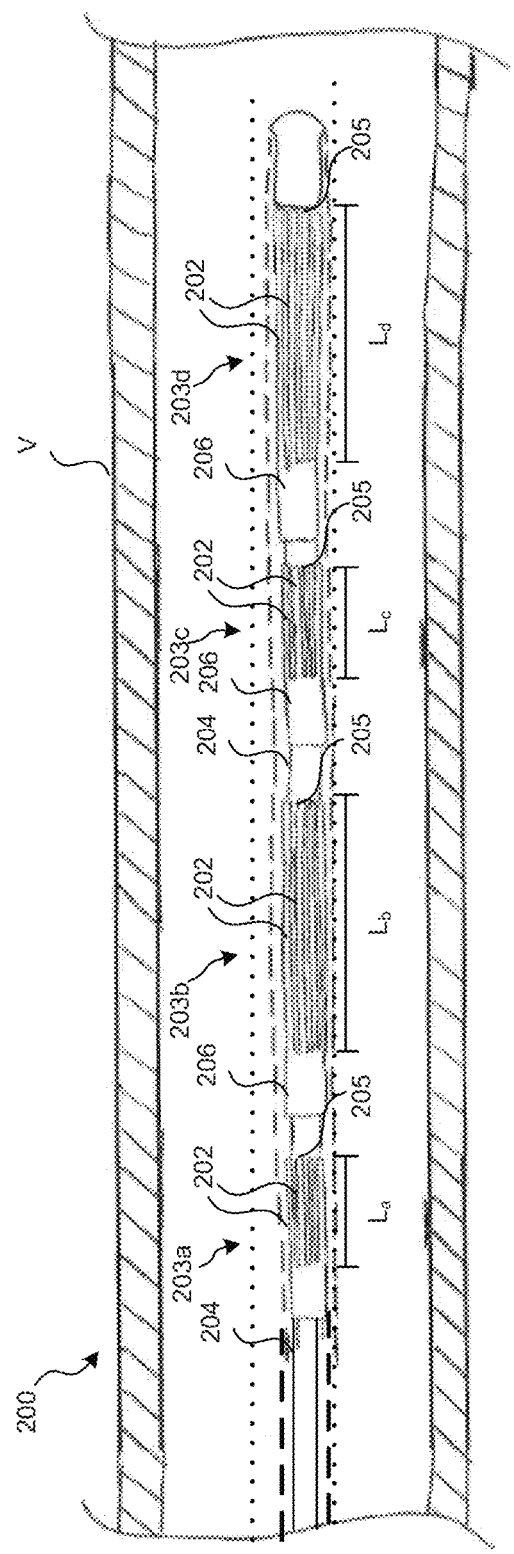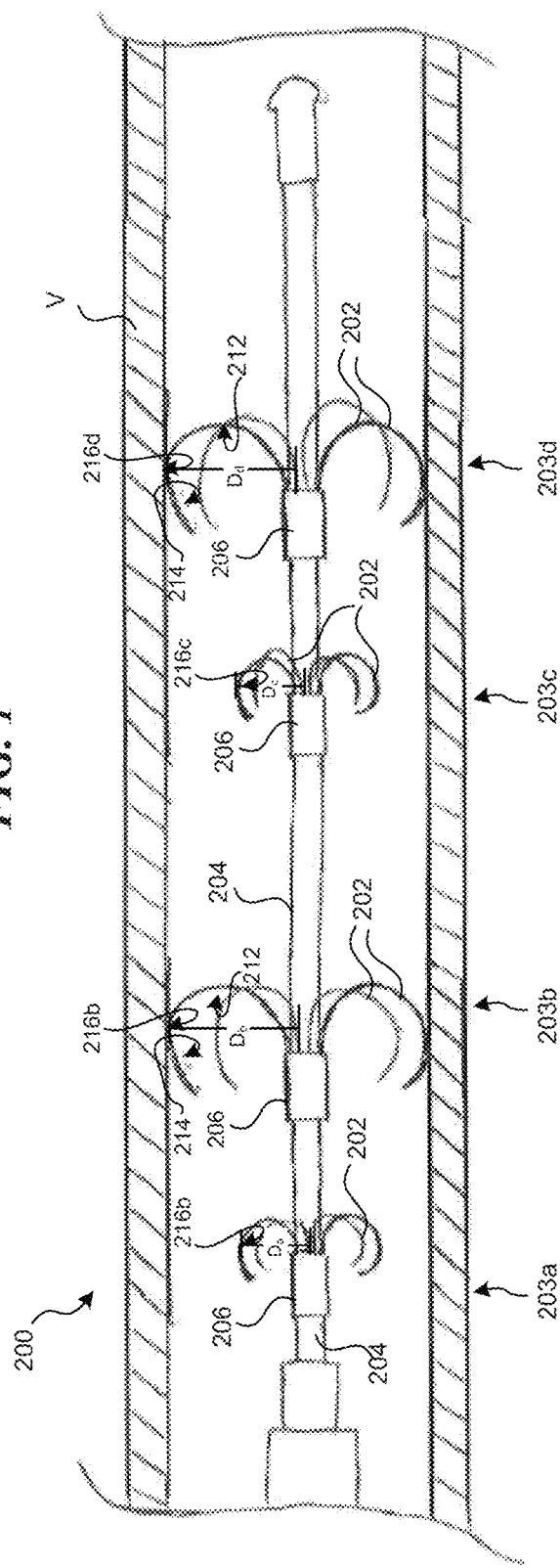
FIG. 1
FIG. 2

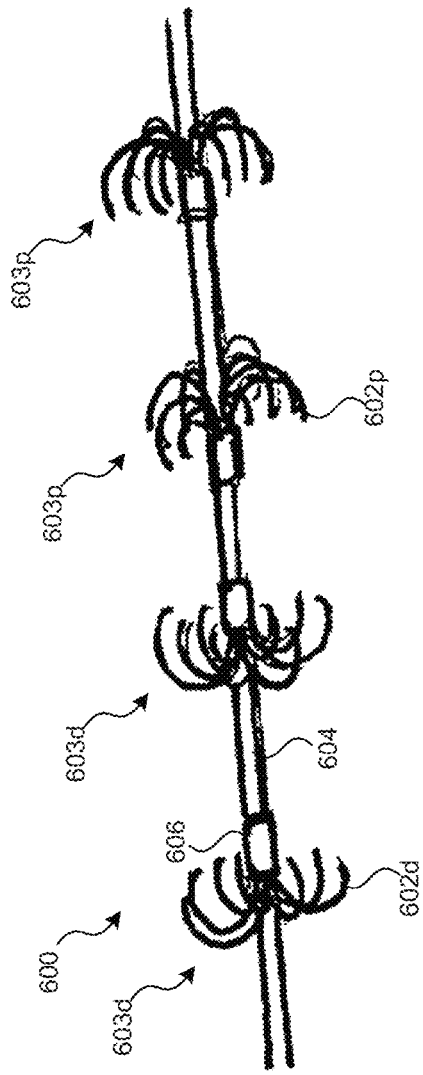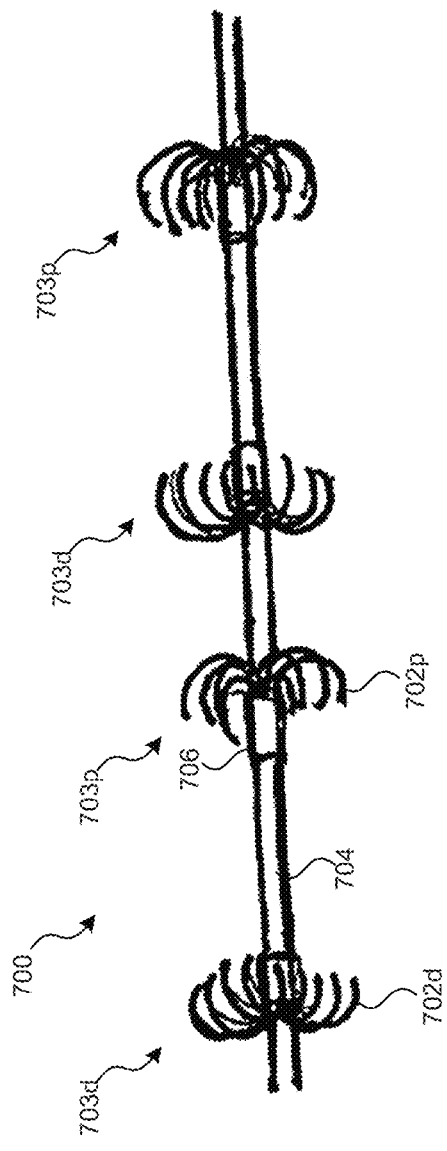

METHODS AND APPARATUS FOR TREATING EMBOLISM

CROSS-REFERENCE TO RELATED APPLICATIONS

This is a continuation of U.S. patent application Ser. No. 16/224,193, filed Dec. 18, 2018, which is a continuation of U.S. patent application Ser. No. 15/031,102, filed Apr. 21, 2016, now issued as U.S. Pat. No. 10,238,406, which is a 35 U.S.C. § 371 U.S. National Phase Application of International Application No. PCT/US2014/061645, filed Oct. 21, 2014, which is a continuation-in-part of U.S. patent application Ser. No. 14/299,933, filed Jun. 9, 2014, now issued as U.S. Pat. No. 9,259,237, and a continuation-in-part of U.S. patent application Ser. No. 14/299,997, filed Jun. 9, 2014, which claims benefit U.S. Provisional Patent Application No. 61/949,953, filed Mar. 7, 2014, and U.S. Provisional Patent Application No. 61/893,859, filed Oct. 21, 2013, each of which is incorporated herein by reference in its entirety.

TECHNICAL FIELD

The present technology relates generally to devices and methods for intravascular treatment of emboli within a blood vessel of a human patient.

BACKGROUND

Thromboembolism occurs when a thrombus or blood clot trapped within a blood vessel breaks loose and travels through the blood stream to another location in the circulatory system, resulting in a clot or obstruction at the new location. When a clot forms in the venous circulation, it often travels to the lungs via the heart and lodges within a pulmonary blood vessel PV causing a pulmonary embolism PE. A pulmonary embolism can decrease blood flow through the lungs, which in turn causes decreased oxygenation of the lungs, heart and rest of the body. Moreover, pulmonary embolisms can cause the right ventricle of the heart to pump harder to provide sufficient blood to the pulmonary blood vessels, which can cause right ventricle dysfunction (dilation), and heart failure in more extreme cases.

Conventional approaches to treating thromboembolism and/or pulmonary embolism include clot reduction and/or removal. For example, anticoagulants can be introduced to the affected vessel to prevent additional clots from forming, and thrombolytics can be introduced to the vessel to at least partially disintegrate the clot. However, such agents typically take a prolonged period of time (e.g., hours, days, etc.) before the treatment is effective and in some instances can cause hemorrhaging. Transcatheter clot removal devices also exist, however, such devices are typically highly complex, prone to cause trauma to the vessel, hard to navigate to the pulmonary embolism site, and/or expensive to manufacture. Conventional approaches also include surgical techniques that involve opening the chest cavity and dissecting the pulmonary vessel. Such surgical procedures, however, come with increased cost, procedure time, risk of infection, higher morbidity, higher mortality, and recovery time. Accordingly, there is a need for devices and methods that address one or more of these deficiencies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1 is a side view of one embodiment of a clot treatment device in a low-profile or delivery state positioned in a blood vessel and configured in accordance with the present technology.

FIG. 2 is a side view of the clot treatment device shown in FIG. 1 in an unrestricted expanded or deployed state positioned in a blood vessel and configured in accordance with the present technology.

FIG. 6 is a side perspective view of a clot treatment device in a deployed state configured in accordance with another embodiment of the present technology.

FIG. 7 is a side perspective view of a clot treatment device in a deployed state configured in accordance with another embodiment of the present technology.

DETAILED DESCRIPTION

Figure 3:
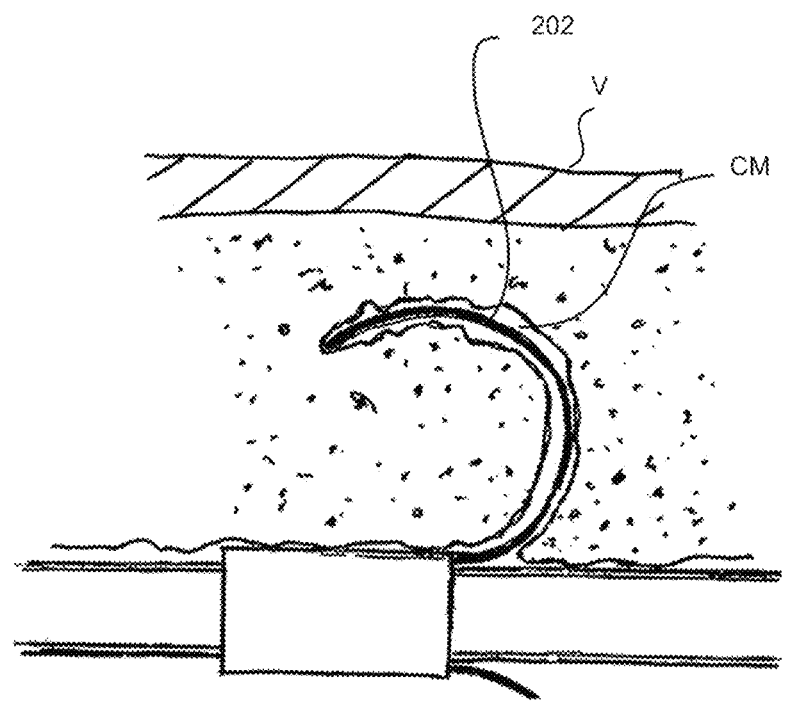
FIG. 3 is a partial side view of the clot treatment device shown in FIG. 2 showing an isolated, deployed clot engagement member within an embolism.

Specific details of several embodiments of clot treatment devices, systems and associated methods in accordance with the present technology are described below with reference to FIGS. 1-14. Although many of the embodiments are described below with respect to devices, systems, and methods for treating an embolism, other applications and other embodiments in addition to those described herein are within the scope of the technology. Additionally, several other embodiments of the technology can have different states, components, or procedures than those described herein. Moreover, it will be appreciated that specific elements, substructures, advantages, uses, and/or other features of the embodiments described with reference to FIGS. 1-14 can be suitably interchanged, substituted or otherwise configured with one another in accordance with additional embodiments of the present technology. Furthermore, suitable elements of the embodiments described with reference to FIGS. 1-14 can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-14.

With regard to the terms "distal" and "proximal" within this description, unless otherwise specified, the terms can reference a relative position of the portions of a clot treatment device and/or an associated delivery device with reference to an operator and/or a location in the vasculature.

I. Selected Embodiments of Clot Treatment Devices

FIG. 1 is a side view of one embodiment of a clot treatment device 200 ("the device 200") in a low-profile or delivery state positioned in a blood vessel V, and FIG. 2 is a side view of the device 200 in an unrestricted expanded or deployed state that is well suited for removing clot material from a blood vessel (e.g., a pulmonary blood vessel). Referring to FIGS. 1 and 2 together, the device 200 can include a support member 204 and a plurality of treatment portions (referred to collectively as treatment portions 203, referred to individually as first-fourth treatment portions 203a-d, respectively) spaced apart along the support member 204. Each treatment portion 203 can include a hub 206 positioned around the support member 204 and a plurality of clot engagement members 202 integral with and extending distally from the corresponding hub 206 to a distal free end 205. As such, individual treatment portions 203 can include a plurality of clot engagement members 202 positioned about the circumference of the support member 204. Although four treatment portions 203 are shown in FIGS. 1 and 2, in other embodiments the clot treatment device can include more or fewer than four treatment portions 203 (e.g., two treatment portions, three treatment portions, five treatment portions, etc.).

In the delivery state shown in FIG. 1 the clot engagement members 202 can be generally linear and extend generally parallel to the support member 204. The distal ends 205 of the clot engagement members 202 are accordingly the distal-most portion of the clot engagement members 202 in the delivery state. In the expanded state, as shown in FIG. 2, the clot engagement members 202 can project radially outwardly relative to the support member 204 in a curved shape. The clot engagement members 202 can have a proximally facing section 212 which defines a proximally facing concave portion, and, in some embodiments, the clot engagement members 202 can further include an end section 214 that curves radially inwardly from the proximally facing section 212. When deployed within a blood vessel adjacent to clot material, the clot engagement members 202 are configured to penetrate the clot material along an arcuate path and hold clot material to the device 200.

In some embodiments the treatment portions 203 can be fabricated from a single tube (e.g., a hypotube). A plurality of elongated slits may be cut or machined through the wall of the tube by various means known in the art (e.g., conventional machining, laser cutting, electrical discharge machining, photochemical machining, etc.) to form a plurality of clot engagement members 202 that are integral with the corresponding hub 206. In some embodiments, the tube can be cut such that individual clot engagement members 202 can have non-circular cross-sections. The cut tube may then be formed by heat treatment to move from the delivery state shown in FIG. 1 to the deployed state shown in FIG. 2 in which the arcuate clot engagement members 202 project radially outward. As is known in the art of heat setting, a fixture or mold may be used to hold the structure in its desired final configuration and subjected to an appropriate heat treatment such that the clot engagement members 202 assume or are otherwise shape-set to the desire arcuate shape. In some embodiments, the device or component may be held by a fixture and heated to about 475-525° C. for about 5-15 minutes to shape-set the structure. In some embodiments, the treatment portions 203 can be formed from various metals or alloys such as Nitinol, platinum, cobalt-chrome alloys, 35N LT, Elgiloy, stainless steel, tungsten or titanium.

Referring still to FIGS. 1-2, the clot engagement members 202 of different treatment portions 203 can have different lengths (referred to collectively as L, referred to individually as first-fourth lengths $L_a$-$L_b$) in the delivery state (FIG. 1) and thus can extend different distances D from the support member 204 in the deployed state (FIG. 2). As such, deployment of the clot engagement members 202 self-centers the device within the blood vessel V and forces the stiffer, shorter clot engagement members 202 to be positioned radially farther from the vessel wall V. As used herein, "shorter clot engagement members" or "shorter treatment portions" refers to clot engagement members 202 and/or treatment portions 203 with lesser lengths L and/or distances D relative to the other clot engagement members 202 and/or treatment portions 203 of the same clot treatment device, and "longer clot engagement members" or "longer treatment portions" refers to clot engagement members 202 and/or treatment portions 203 with greater lengths L and/or distances D relative to the other clot engagement members 202 and/or treatment portions 203 of the same clot treatment device.

For example, as shown in FIG. 1, in the delivery state, the first treatment portion 203a can have clot engagement members with a first length $L_a$, the second treatment portion 203b can have clot engagement members 202 with a second length $L_b$, the third treatment portion 203c can have clot engagement members 202 with a third length $L_c$, and the fourth treatment portion 203d can have clot engagement members 202 with a fourth length $L_d$. In FIG. 1, the clot engagement member lengths L of adjacent treatment portions 203 alternate between shorter and longer clot engagement members (i.e., clot engagement members 202 of first and third treatment portions 203a, 203c alternate with clot engagement members 202 of the second and fourth treatment portions 203b, 203d along the support member 204). In other words, in the embodiment shown in FIG. 1, the first length $L_a$ is less than the second length $L_b$, the second length $L_b$ is greater than the third length $L_c$, and the third length $L_c$ is less than the fourth length $L_d$. In other embodiments, the clot treatment device 200 and/or treatment portions 203 can have other suitable configurations and/or arrangements. For example, the clot treatment device 200 can include any arrangement of treatment portions 203 having shorter clot engagement members 202 and treatment portions 203 having longer clot engagement members 202 relative to the shorter clot engagement members 202. Moreover, the clot treatment device 200 can have any number of treatment portions 203 having shorter clot engagement members 202 and/or any number of treatment portions 203 having longer clot engagement members 202. Also, clot engagement members 202 having varying lengths need not be in separate treatment portions 203. For example, in some embodiments, one or more treatment portions 203 can include both shorter and longer clot engagement members 202 in the same treatment portion 203.

Referring to FIG. 2, in the deployed state, the clot treatment device 200 can include a first treatment portion 203a having clot engagement members 202 with a radially furthest apex 216a that is a first distance $D_a$ from the support member 204, a second treatment portion 203b having clot engagement members 202 with a radially furthest apex 216b that is a second distance $D_b$ from the support member 204, a third treatment portion 203c having clot engagement members 202 with a radially furthest apex 216c that is a third distance $D_c$ from the support member 204, and a fourth treatment portion 203d having clot engagement members 202 with a radially furthest apex 216d that is a fourth distance $D_d$ from the support member 204. As shown in FIG. 2, the distance D of the radially furthest apex of adjacent treatment portions 203 from the support member 204 can alternate between shorter (clot engagement members 202 of first and third treatment portions 203a, 203c) and longer (clot engagement members 202 of the second and fourth treatment portions 203b, 203d). In other words, in the embodiment shown in FIG. 1, the first distance $D_a$ is less than the second distance $D_b$, the second distance $D_b$ is greater than the third length $D_c$, and the third distance $D_c$ is less than the fourth distance $D_d$. In other embodiments, the clot treatment device 200 and/or treatment portions 203 can have other suitable configurations and/or arrangements. For example, the clot treatment device 200 can include any arrangement of treatment portions 203 having clot engagement members 202 with longer or shorter radially furthest apex distances D. Moreover, the clot treatment device 200 can have any number of treatment portions 203 having shorter clot engagement member radially furthest apex distances D and/or any number of treatment portions 203 having longer clot engagement members radially furthest apex distances D. Also, clot engagement members 202 having varying radially furthest apex distances D need not be in separate treatment portions 203. For example, in some embodiments, one or more treatment portions 203 can include engagement members 202 with both shorter radially furthest apex distances D and longer radially further apex distances D.

Advantageously, clot engagement members 202 having shorter radially furthest apex distances D and/or shorter lengths L can have a greater radial stiffness than clot engagement members 202 having longer radially furthest apex distances D and/or longer lengths L. As shown in the isolated side view of a clot engagement member of FIG. 3, when deployed, the shorter, stiffer clot engagement members 202 can thus be spaced apart from the vessel wall V and grasp a more central portion of the clot material to provide mechanical resilience during withdrawal of the clot material CM while the apices of the longer, more flexible clot engagement members 202 (not shown in FIG. 3) atraumatically engage and slide along the vessel wall V. In some embodiments, the stiffness of the shorter clot engagement members 202 may be from about 150% to about 400% greater than the stiffness of the longer clot engagement members 202. In some embodiments, the type of material, cross-sectional shape and/or area of the individual clot engagement members 202 can also be varied to affect the radial stiffness of the clot engagement members 202. For example, the relatively shorter clot engagement members 202 can be made from a first material and the relatively longer clot engagement members 202 can be made from a second material that is more ductile, elastic, and or flexible than the first material, and/or the shorter clot engagement members 202 can have a great cross-sectional thickness or area than the relatively longer clot engagement members 202.

The clot engagement members 202 can have a single or constant radius of curvature. In other embodiments, the clot engagement members 202 can have a plurality of radii of curvature, such as a first region with a first radius of curvature and a second region with a second radius of curvature. In some embodiments, the clot engagement members 202 can have a single radius of curvature that is the same for all of the clot engagement members 202. In other embodiments, the clot treatment device 200 can have a first group of clot engagement members 202 with a constant radius of curvature and a second group of clot engagement members 202 with a plurality of radii of curvature. Moreover, in additional embodiments the clot treatment device 200 can include a first group of clot engagement members 202 having a first radius of curvature and a second group of clot engagement members 202 having a second radius of curvature different than the first radius of curvature. In some embodiments, the radius of the clot engagement members 202 can be between about 1.5 mm and about 12 mm, and in some embodiments, between about 2 mm and about 12 mm.

Figure 4:
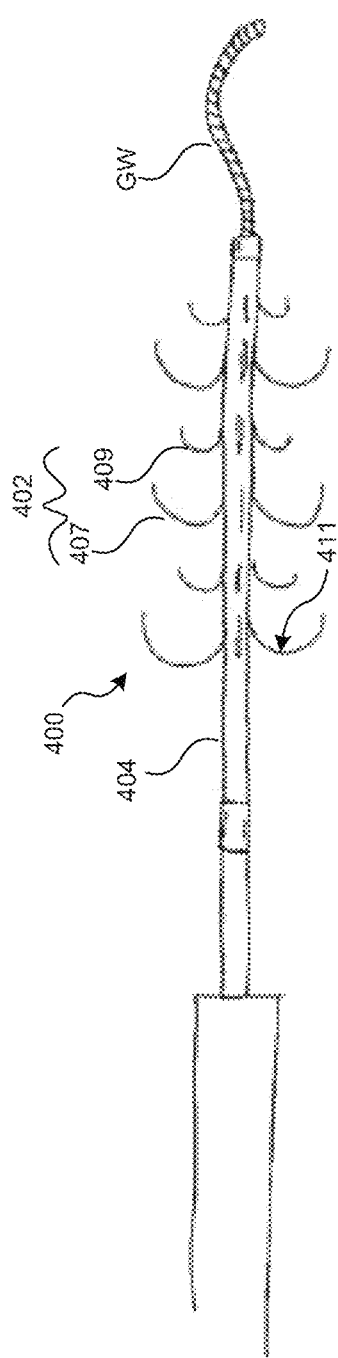
FIG. 4 is a side view of a clot treatment device having distally-facing clot engagement members in a deployed state configured in accordance with another embodiment of the present technology.

FIG. 4 is a side view of another embodiment of a clot treatment device 400 in a deployed state configured in accordance with the present technology. As shown in FIG. 4, the clot treatment device 400 can include a support member 404 and a plurality of clot engagement members 402 positioned about the support member 404. The support member 404 can be an elongated tubular structure that includes a lumen configured to slidably receive a guidewire GW therethrough. As shown in FIG. 4, in the deployed state, the clot engagement members 402 can extend radially outward from the support member 404 and curve distally such that individual clot engagement members 402 include a concave, distally-facing portion 411.

The clot engagement members 402 can be arranged in rows such that adjacent rows along the support member 404 alternate between long 407 and short 409 clot engagement members. Additionally, the short clot engagement members 409 can be circumferentially aligned with the long 407 clot engagement members 407 about the support member 404. In other embodiments, the clot engagement members 402 can have other suitable arrangements and/or configurations. For example, in some embodiments, one or more of the short clot engagement members 409 can be circumferentially offset from one or more of the long clot engagement members 409 about the support member 404, the long and short clot engagement members 407, 409 can be within the same rows, additionally or alternatively arranged in columns, and/or randomly positioned along or about the support member 404.

Figure 5:
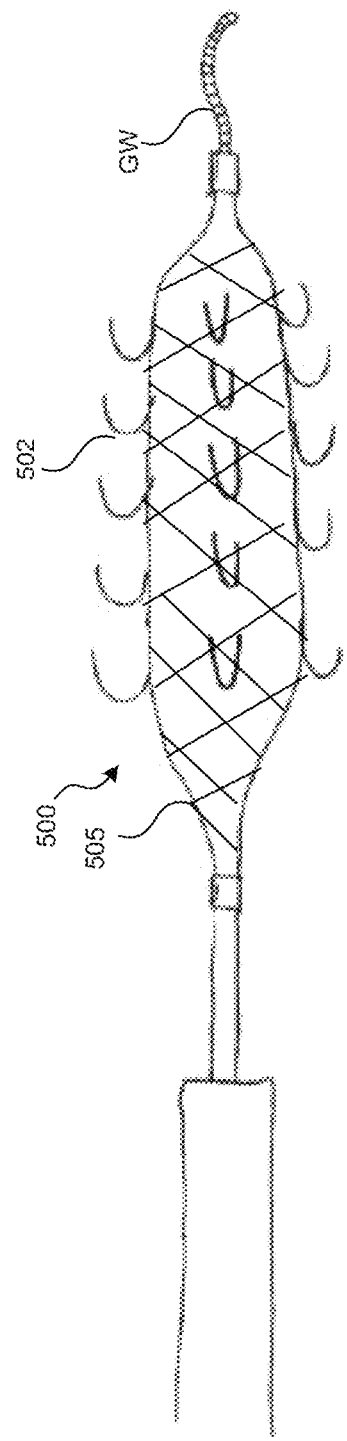
FIG. 5 is a side view of a clot treatment device having distally-facing clot engagement members in a deployed state configured in accordance with another embodiment of the present technology.

FIG. 5 is a side view of another embodiment of a clot treatment device 500 in a deployed state configured in accordance with the present technology. As shown in FIG. 5, the clot treatment device 500 can include an expandable mesh 505 and a plurality of arcuate clot engagement members 502 extending radially outwardly from the expandable mesh 505. Although only distally-facing clot engagement members 502 are shown in FIG. 5, in other embodiments, the clot treatment device 500 can additionally or alternatively include proximally-facing clot engagement members (such as those shown in FIGS. 1-2 and FIG. 3). In some embodiments, the clot engagement members 502 can be interwoven into the mesh structure 505. In other embodiments, the clot engagement members 502 can also be bonded, soldered, welded, tied or otherwise secured and/or mechanically interlocked to the mesh 505.

In certain procedures, it may be advantageous to move the clot treatment device along the vessel (fully or partially within the embolism) in both the upstream and downstream directions to facilitate engagement and/or disruption of a clot or thrombus by the clot engagement members. During such procedures, it may be advantageous to include one or more distally-facing clot engagement members to enhance engagement and/or disruption of the clot material. Accordingly, the clot treatment devices of the present technology can include both proximally-facing clot engagement members and distally-facing clot engagement members. For example, FIG. 6 is a perspective side view of a portion of a clot treatment device 600 having proximally-facing (e.g., concave proximally) treatment portions 603p (collectively referred to as treatment portions 603) comprised of proximally-facing 602p clot engagement members and distally-facing (e.g., concave distally) treatment portions 603d comprised of distally-facing 602d clot engagement members. As shown in FIG. 6, the distally-facing clot engagement members 602d of the distally-facing treatment portions 603d extend radially outwardly from the corresponding hub 606, then curve distally to a distal free-end. Although the clot treatment device 600 shown in FIG. 6 includes two distally-facing treatment portions 603d and two proximally-facing treatment portions 603p along the support member 604, the clot treatment device 600 can include any arrangement and/or configuration of treatment portions and/or clot engagement members. For example, as shown in the clot treatment device 700 of FIG. 7, the adjacent treatment portions can alternate between those including proximally-facing clot engagement members 702p and distally-facing clot engagement members 703d.

Figure 8:
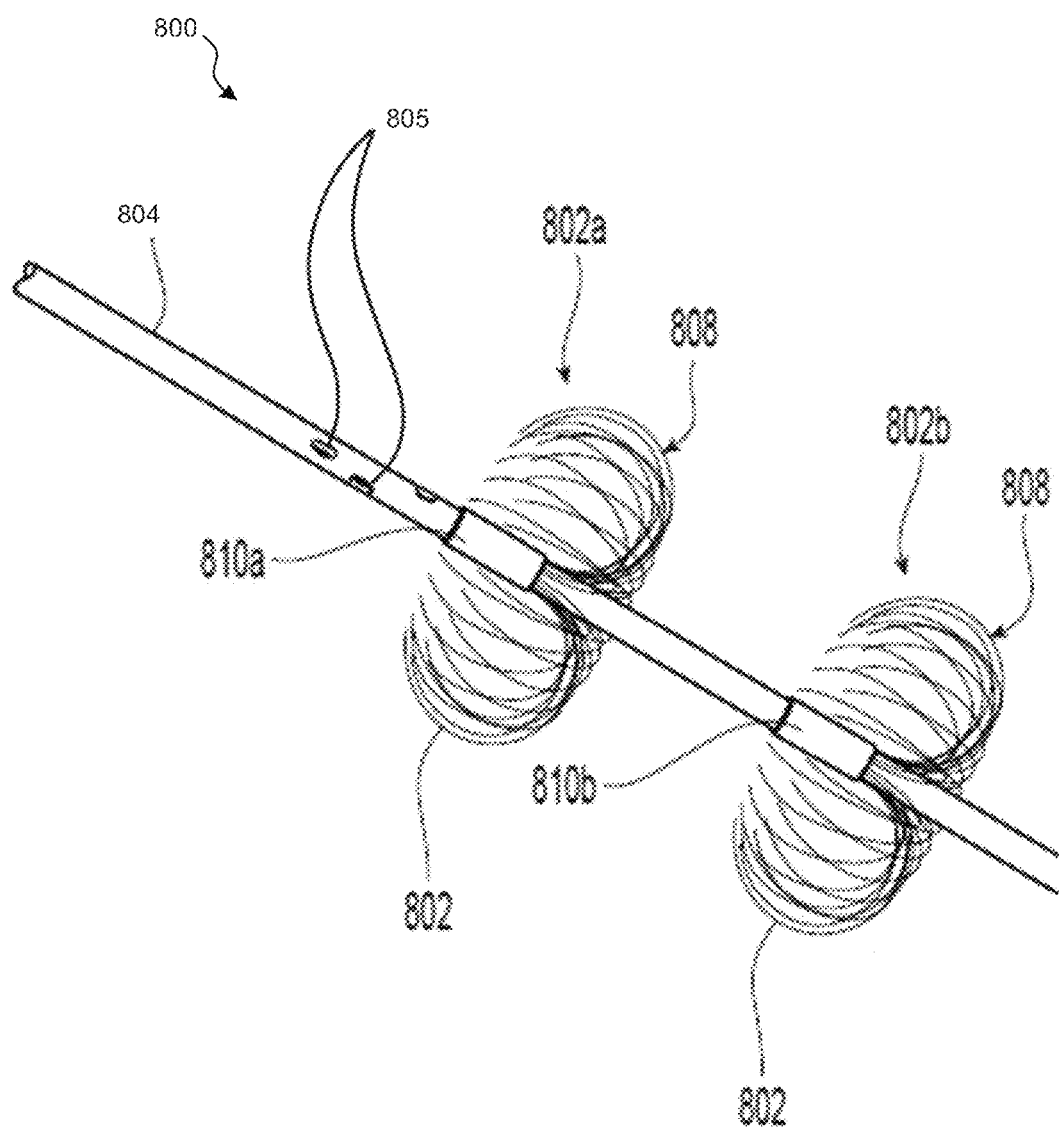
FIG. 8 is a side perspective view of a portion of a clot treatment device in a deployed state having a plurality of ports configured in accordance with another embodiment of the present technology.

FIG. 8 is a side perspective view of a portion of another embodiment of a clot treatment device 800 configured in accordance with the present technology. As shown in FIG. 8, the support member 804 of the clot treatment device 800 can include holes or ports 805 to allow the infusion of fluids (e.g., thrombolytics) along its length and between treatment portions (labeled 802a and 802b). The ports 805 can be positioned anywhere along the length of the support member 804 (e.g., proximal to the proximal-most treatment portion, distal to the distal-most treatment portion, in between treatment portions, etc.). The location of the ports 805 along the length of the support member 804 can enhance the direct infusion of the fluids into the clot and improve the biologic action and effectiveness of such drugs. Additionally, in some embodiments, the clot engagement members can be at least partially hollow and/or include ports or inlets along their lengths and/or at their free-ends.

Figure 9A:
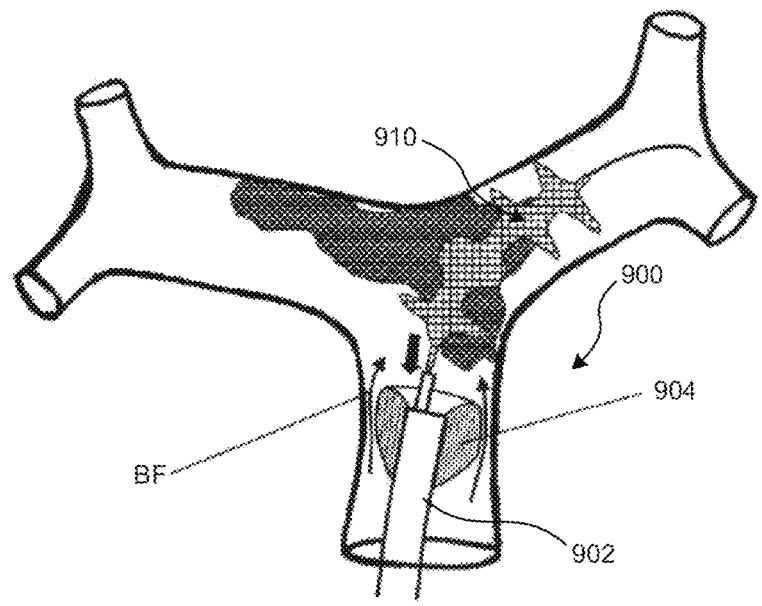
FIG. 9A is a front view of a portion of a delivery system for a clot treatment device that includes an expandable member in a deployed state configured in accordance with an embodiment of the present technology.
Figure 9B:
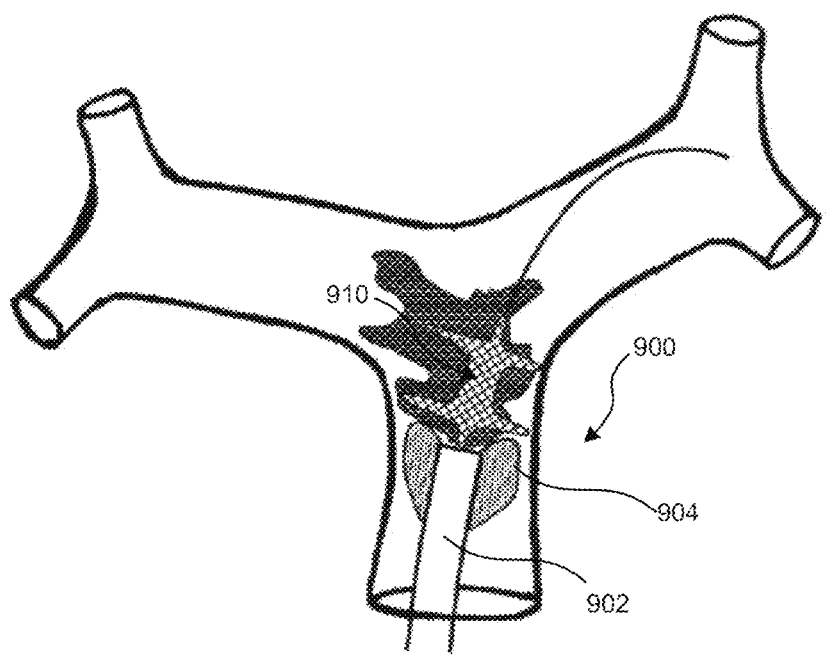
FIG. 9B is a front view of a portion of a delivery system for a clot treatment device that includes an expandable member in a deployed state configured in accordance with another embodiment of the present technology.

II. Additional Embodiments of Clot Treatment Devices and Associated Devices, Systems and Methods FIG. 9 is a front view of a delivery system 900 for use with the clot treatment devices of the present technology. As shown in FIG. 9, the delivery system 900 can include a guide-catheter 902 and an expandable member 904 (e.g., a balloon) coupled to a distal portion of the guide-catheter 902. In such embodiments, the expandable member 904 can be expanded to a diameter less than the vessel diameter, as shown in FIG. 9. Use of the expandable member 904 coupled to the distal portion of the guide catheter 902 can divert flow in the vessel away from the distal portion of the guide catheter 902, thereby reducing or eliminating the possibility of clot material traveling proximal of the device during retraction of the clot treatment device 910 (and adherent clot) into the guide catheter 902 (shown in FIG. 9B). Moreover, the use of an expandable member 904 with the guide catheter 902 can be advantageous as the expandable member 904 can form a funnel adjacent to the distal end of the guide catheter 904, thereby facilitating retraction of the clot material into the guide catheter 904. Additionally, expanding the expandable member 904 to a diameter that is less than the diameter allows some blood flow BF to occur through the vessel near the treatment site, thus reducing any risk associated with complete blockage of blood flow.

Figure 10A:
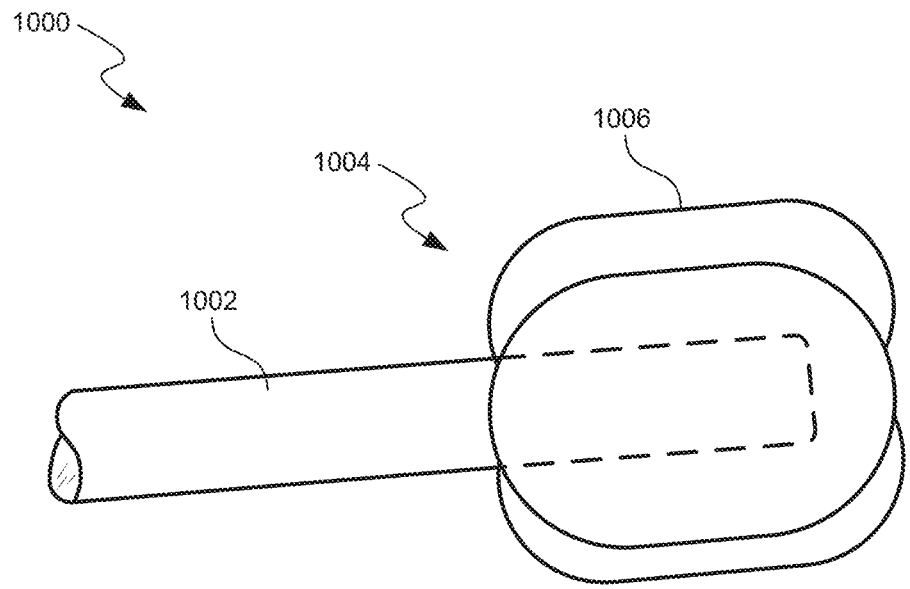
FIG. 10A is a side view of an expandable member configured in accordance with the present technology.
Figure 10B:
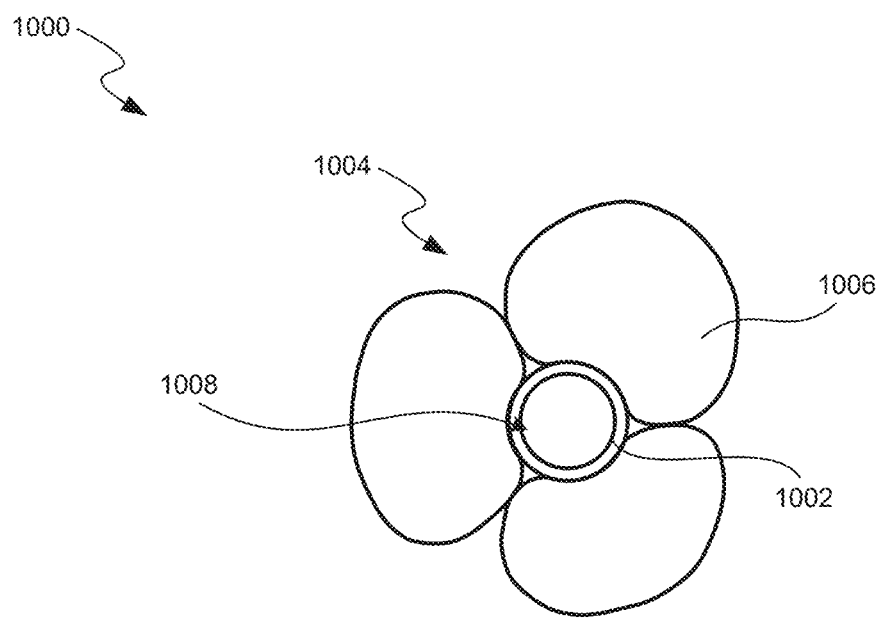
FIG. 10B is an end view of the expandable member shown in FIG. 10A.

FIG. 10A is a side view of a portion of a delivery system 1000 for use with the clot treatment devices of the present technology, and FIG. 10B is a top view of the delivery system shown in FIG. 10A. Referring to FIGS. 10A and 10B together, in those embodiments that include expandable members coupled to a distal portion of the guide catheter, the expandable member can center the guide catheter within the vessel, thereby enhancing and/or facilitating clot removal and/or aspiration. Since the clot treatment device is self-expanding, it will generally tend to self-center within the blood vessel in addition to the centering of the guide catheter enabled by the expandable members of the delivery system. Alignment of the guide catheter and clot treatment device will provide the best situation for guiding of clot to the distal end of the catheter with the least amount of shearing of clot by the distal end of the catheter. Thus, general alignment of the clot treatment device and the guide catheter may improve the efficiency and quality of clot extraction and/or clot aspiration and thereby reduce breakup of the clot and distal embolization. In some embodiments, a multi-lobed expandable member may be used to center the guide catheter within the blood vessel while allowing some blood flow past the expandable members so as to not completely occlude the blood vessel during the procedure. Various multi-lobed expandable member configurations are known in the art including but not limited to a tri-lobed expandable member as shown in FIGS. 10A and 10B.

Figures 11A, 11B:
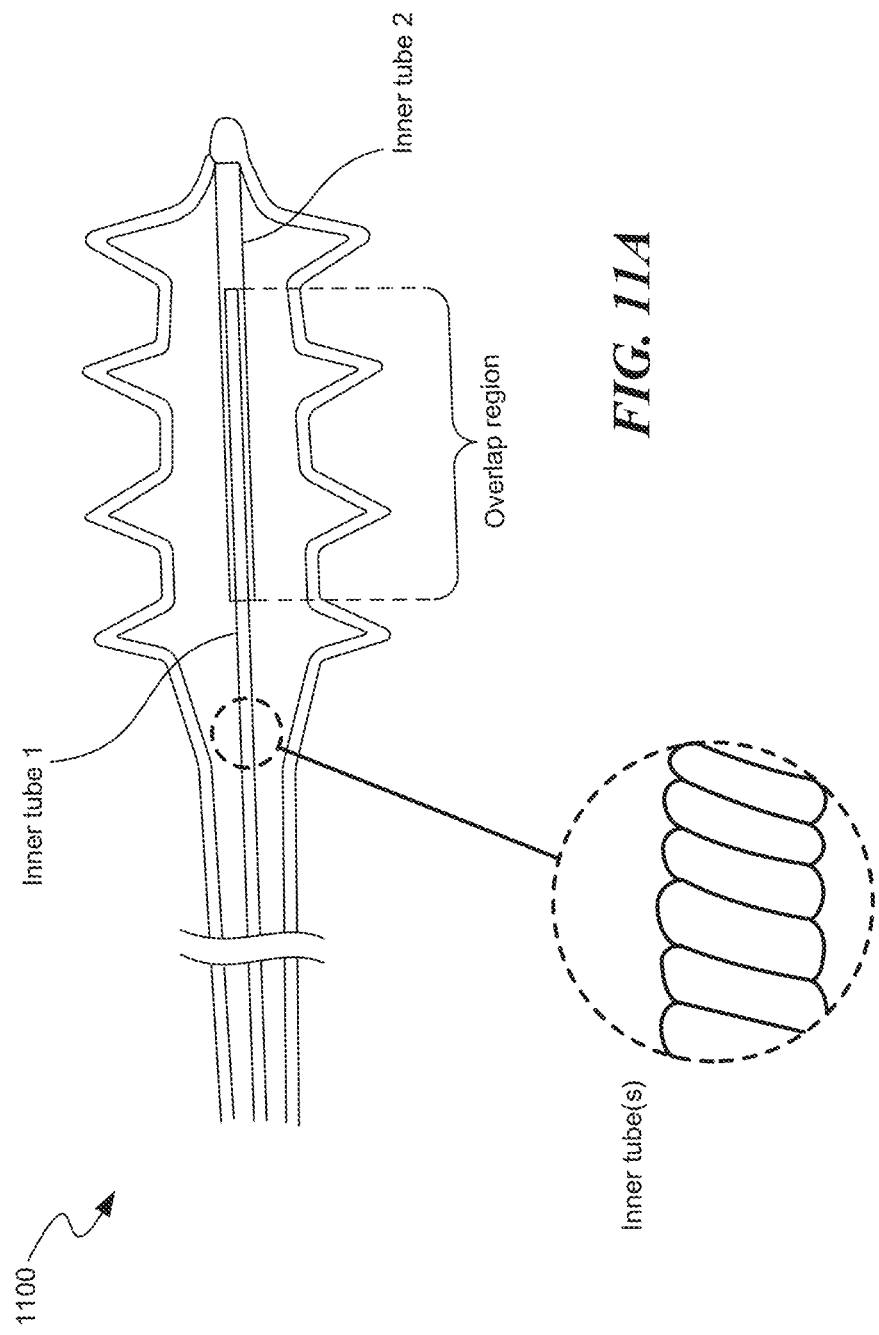
FIG. 11A is a side cross-sectional view of a clot treatment device configured in accordance with the present technology.
FIG. 11B is an expanded, isolated view of a portion of the clot treatment device shown in FIG. 11A.

In any of the clot treatment device embodiments that comprise a central tube member, the inner tube or "tether tube" may be constructed so as to have spring properties. For example, as shown in FIGS. 11A and 11B, the tube may be a coil or spiral cut tube so that when tension is applied, it readily elongates. A spring inner tube member may provide improved self-expansion while still providing a lumen for a guidewire, catheter or the like to be inserted therethrough. Moreover, the inner tube or "tether tube" may be constructed with a first proximal tube that is attached to the clot treatment device proximal to the radially expanding segment and a second distal tube that is attached to the clot treatment device distal to the radially expanding segment. One tube may be larger in diameter than the other so that they may be over-lapped with a portion where the smaller tube is coaxial within the larger tube and thus "telescoped" as shown in FIGS. 11A and 11B. In this telescoped configuration, the tubes may slide freely relative to each other. Thus, with a telescoped inner tube configuration, a guidewire lumen is maintained while allowing a large elongation without plastic deformation.

Figure 12:
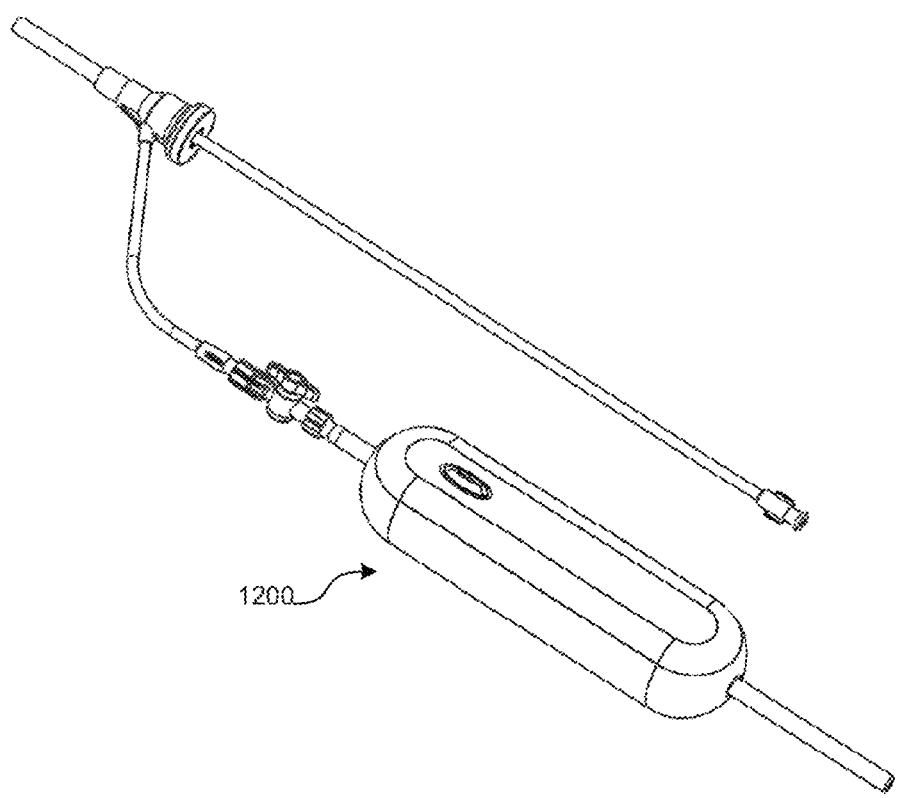
FIG. 12 is a pressure-generating member configured in accordance with the present technology.
Figure 14:
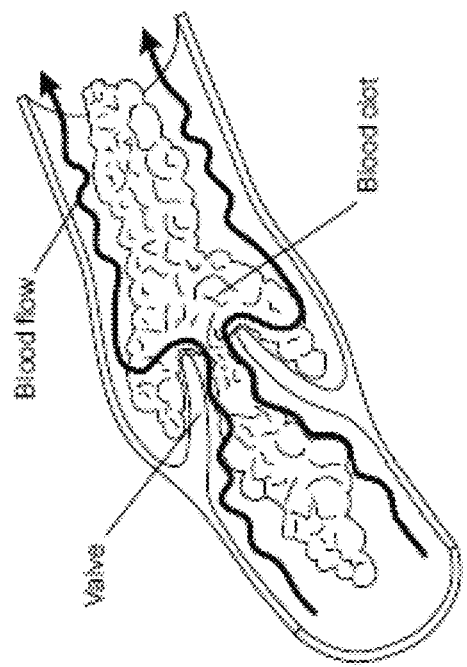
FIG. 14 is an enlarged schematic representation of a deep vein thrombosis.
Figure 13:
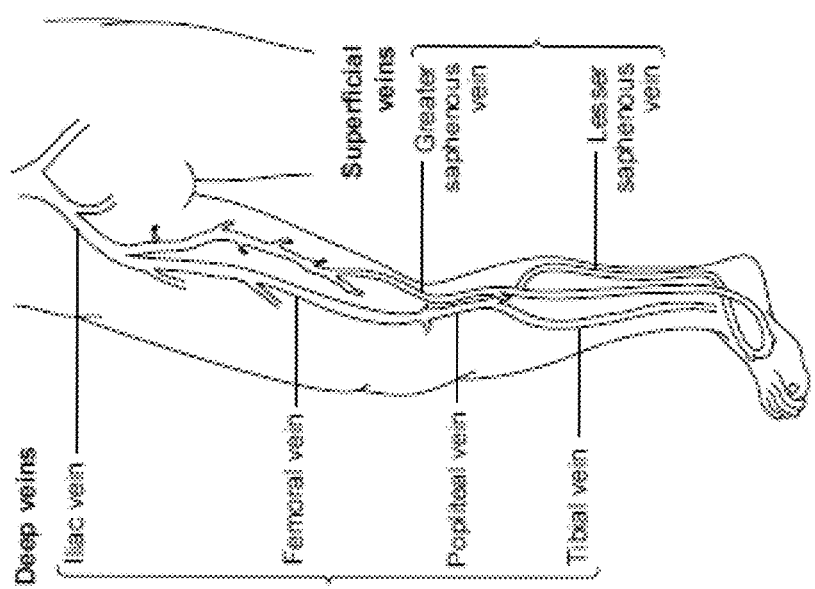
FIG. 13 is a schematic representation of the venous system of a human leg.

Now referring to FIG. 12, in some embodiments, parts of the system that retract and/or aspirate fluid and debris may be automated. For example, the movement of the pump (e.g. syringe) plunger may have a mechanism such as a linear actuator, drive screw or the like to effect movement under electronic control. Likewise, the linear movement of the device and delivery catheter for deployment and/or retraction may also be operated by a mechanism. In some embodiments, both the pump and the catheter and device movements may be mechanized and synchronized. In addition, sensors may be incorporated into the system on either the device and/or catheters such that the system will automatically turn mechanisms on/off as desired. This automation may be further controlled by a programmable controller, computer or electronics and software as is well-known in the art of automation. In some embodiments, the system may automatically shut off aspiration when a predetermined amount of device retraction has taken place. That way, the amount of blood that is aspirated is limited. In some embodiments, a continuously aspirating pump mechanism rather than the discrete pump (e.g. syringe) as described herein may be used. The use of a foot petal, a hand switch or an automated or sensor actuated control to limit the duration of a continuous pump may allow smooth continuous aspiration during device retraction without excessive blood being removed from the patient. This may be accomplished by having the pump operate for a relatively short duration or pulses. In some embodiments, the pump may operate for less than about 15 seconds and in other embodiments less that about 5 seconds. A diagram of such a system with a continuous aspiration pump is shown in Figure F. In some embodiments, a method of synchronized device retraction and aspiration is described wherein less than about 500 cc of blood and debris are removed from the patient. In other embodiments, the device may be retracted with aspiration of between about 50 cc and 400 cc, in some embodiments less than about 200 cc and in some embodiments less than about 100 cc of blood and debris.

III. Pertinent Anatomy and Physiology

Some embodiments described here may be particularly useful for the treatment of deep vein thrombosis. (See FIGS. 13 and 14). Deep vein thrombosis (DVT) is a medical condition that results from the formation of a blood clot, or thrombus, within a vein. Thrombi may develop in the veins of the calves, legs, arms, pelvis or abdomen, but they may occur in other locations as well. The clot is typically formed from a pooling of blood within the vein due to abnormally long periods of rest or inactivity, e.g. when an individual is bed ridden following surgery or suffering a debilitating illness or during extended airline flights. The propensity to form clots can be also be influenced by other factors including, coagulation disorders, the presence of cancer, dehydration, hormone replacement therapy, use of birth control pills, genetic deficiencies, autoimmune disorders, and endothelial cell injury and trauma, etc. Thrombi are likely to form at the location of a stenosis (e.g., an unnatural narrowing of an artery). Clots often form near the venous valves; one-way valves that prevent the back-flow of blood as it returns to the right heart (blood is squeezed up the leg against gravity and the valves prevent it from flowing back to our feet). Clinical sequelae of DVT are significant in both the acute and chronic settings. Initial consequences include acute lower-extremity symptoms, risk of pulmonary emboli (PE) and death. Long-term consequences include recurrent DVT, lower-extremity venous hypertension, claudication, pain, swelling and ulceration, which can result in significant post-thrombotic morbidity. Potentially thromboembolic DVT usually arises in one of the large deep veins of the lower limb (e.g. iliac and femoral veins). Patients with iliofemoral DVT tend to have marked pain and swelling and up to 50% experience pulmonary embolism.

Percutaneous access for endovascular interventions is most often achieved in the vein distal to the occluded segment. For isolated iliac DVT, an ipsilateral common femoral puncture is most appropriate. Alternatively, a retrograde approach from either the jugular, iliac vein or the contralateral femoral vein may be used for isolated iliac and femoral vein DVT. More commonly, however, patients present with more extensive iliofemoral or iliofemoral popliteal thrombosis, in which case access is best obtained from the ipsilateral popliteal vein while the patient is positioned prone. Ultrasound guidance may be used for access of the popliteal or tibial veins and for any access obtained while the patient is fully anticoagulated. Further, a micropucture technique with a 22-gauge needle and 0.014-inch guidewire may minimize bleeding complications and vessel wall trauma. Following initial access, the thrombus is crossed with a guidewire to facilitate catheter or device positioning. For a lower puncture location (i.e., closer to the feet) such as the popliteal, a suitable (e.g., less than 10 F) catheter introducer sheath (such as a Flexor® manufactured by Cook, Inc. of Bloomington, Ind.) may be introduced into the vein over a guidewire. If alternate access is done for a retrograde approach to the thrombosis, a larger introducer (up to about 22 F) may be used. If a downstream access is made and then a retrograde approach to the thrombus is done, an expandable tip catheter such as that shown in FIGS. 20 and 21 (PCT/US13/61470) may help prevent clot or debris that may be dislodged or embolized during the procedure from traveling toward the heart. Alternatively, if a lower or upstream access to the vein and then antegrade approach to the thrombus is made, an occlusion device such as a balloon or a filtration/capture device such a distal protection device may be place downstream of the thrombus. For example, a distal protection device may be inserted into the iliac or IVC for a contralateral vein. An exemplary distal protection device is the SpiderFX™ Embolic Protection Device commercially available from Covidien (Plymouth, Minn.).

IV. Examples

The following examples are illustrative of several embodiments of the present technology:

1. A clot treatment device for treating an embolism within a blood vessel, the clot treatment device comprising:

a support member configured to extend through a delivery catheter, wherein the support member has a proximal portion and a distal portion;

a plurality of first clot engagement members positioned about the circumference of the distal portion of the support member, wherein, in the deployed state, individual first clot engagement members extend radially outwardly with respect to the support member and have a curved portion that includes a first radially furthest apex that extends a first radial distance from the support member;

a plurality of second clot engagement members positioned about the circumference of the distal portion of the support member, wherein, in the deployed state, individual second clot engagement members have a curved portion that includes a second radially furthest apex that extends a second radial distance from the support member, and wherein the first radial distance is greater than the second radial distance;

wherein, in the deployed state, individual curved portions of the first and second clot engagement members project radially outwardly relative to the support member in a curve that has a proximally extending section which defines a proximally facing concave portion, and wherein the curved portion of the first and second clot engagement members further includes an end section that curves radially inwardly from the proximally extending section; and wherein the clot engagement members are configured to penetrate clot material along an arcuate path and hold clot material to the clot treatment device.

2. The clot treatment device of example 1, further comprising:

a first hub positioned around the support member at a first location; and a second hub positioned around the support member at a second location spaced apart from the first location along the support member;

wherein— individual first clot engagement members extend from the first hub, wherein a proximal portion of the first clot engagement members are integral with the first hub; and individual second clot engagement members extend from the second hub, wherein a proximal portion of the second clot engagement members are integral with the second hub.

3. The clot treatment device of any of examples 1 or 2 wherein:

at least one of the first radially furthest apices of the individual first clot engagement members are configured to engage the vessel wall in a deployed state; and none of the second radially furthest apices of the individual first clot engagement members are configured to engage the vessel wall in a deployed state.

4. The clot treatment device of any of examples 1-3 wherein the first clot engagement members have a first stiffness and the second clot engagement members have a second stiffness greater than the first stiffness.

5. The clot treatment device of any of examples 1-4 wherein:

the first clot engagement members are positioned about the support member at a first location along the length of the support member; and the second clot engagement members are positioned about the support member at a second location along the length of the support member that is spaced longitudinally apart from the first location along the support member.

6. The clot treatment device of any of examples 1-5, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein the third radial distance is substantially the same as the first radial distance.

7. The clot treatment device of example 6, further comprising:

a plurality of fourth clot engagement members positioned about the circumference of the distal portion of the support member, wherein, in the deployed state, individual fourth clot engagement members extend radially outwardly with respect to the support member and have a curved portion that includes a fourth radially furthest apex that extends a fourth radial distance from the support member; and wherein the fourth radial distance is substantially the same as the second radial distance.

8. The clot treatment device of example 7 wherein:

the first clot engagement members are positioned at a first location along the length of the support member;

the second clot engagement members are positioned at a second location along the length of the support member that is different than the first location;

the third clot engagement members are positioned at a third location along the length of the support member that is different than the first and second locations;

the fourth clot engagement members are positioned at a fourth location along the length of the support member that is different than the first, second, and third locations.

9. The clot treatment device of any of examples 1-5 and 7, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein the third radial distance is different than the second radial distance and the first radial distance.

10. The clot treatment device of any of examples 1-5 and 7, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein, in the deployed state, individual curved portions of the third engagement members project radially outwardly relative to the support member in a curve that has a distally extending section which defines a distally facing concave portion, and wherein the curved portion of individual third engagement members further includes an end section that curves radially inwardly from the distally extending section.

11. A treatment device for treating an embolism within a blood vessel, the clot treatment device moveable between a low-profile undeployed state and a deployed state, the clot treatment device comprising:

a support member configured to extend through a delivery catheter, wherein the support member has a proximal portion and a distal portion;

a plurality of first clot engagement members positioned about the circumference of the distal portion of the support member, wherein, in the undeployed state, individual first clot engagement members are linear and have a first length;

a plurality of second clot engagement members positioned about the circumference of the distal portion of the support member, wherein, in the undeployed state, individual second clot engagement members are linear and have a second length that is less than the first length;

wherein, in the deployed state, the individual first and second clot engagement members project radially outwardly relative to the support member in a curve that has a proximally extending section which defines a proximally facing concave portion, and wherein the clot engagement members are configured to penetrate clot material along an arcuate path and hold clot material to the clot treatment device.

12. The clot treatment device of example 11 wherein the curved portion further includes an end section that curves radially inwardly from the proximally extending section.

13. The clot treatment device of any of examples 11-12 wherein, in the undeployed state:

individual first clot engagement members are positioned parallel to the support member; and individual second clot engagement members positioned parallel to the support member.

14. The clot treatment device of any of examples 11-13, further comprising:

a first hub positioned around the support member at a first location; and a second hub positioned around the support member at a second location spaced apart from the first location along the support member;

wherein— individual first clot engagement members extend distally from the first hub in the undeployed state, wherein a proximal portion of the first clot engagement members are integral with the first hub; and individual second clot engagement members extend distally from the second hub in the undeployed state, wherein a proximal portion of the second clot engagement members are integral with the second hub.

VI. Conclusion

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of treating clot material in a blood vessel, the method comprising:

advancing a clot treatment device in a low-profile state through a lumen of a guide catheter, wherein the clot treatment device includes a mesh structure and a plurality of treatment portions;

at least partially expanding the clot treatment device within the blood vessel from the low-profile state to a deployed state, wherein individual ones of the treatment portions include a proximally-facing curved portion and a distally-facing curved portion in the deployed state, and wherein the proximally-facing curved portion and the distally-facing curved portion have the same radius of curvature;

expanding a funnel member within the blood vessel proximal of the clot material;

engaging the clot treatment device with the clot material;

retracting the clot treatment device and a portion of the clot material into a distal portion of the guide catheter; and inhibiting, with the funnel member, the clot material from moving proximally through the blood vessel past the distal portion of the guide catheter during retraction of the clot treatment device and the portion of the clot material into the distal portion of the guide catheter.

2. The method of claim 1 wherein the method further comprises aspirating the guide catheter.

3. The method of claim 2 wherein aspirating the guide catheter includes actuating a syringe.

4. The method of claim 2 wherein aspirating the guide catheter includes providing discrete pulses of aspiration to the lumen of the guide catheter.

5. The method of claim 1 wherein the method further comprises aspirating the guide catheter during retraction of the clot treatment device and the portion of the clot material into the distal portion of the guide catheter.

6. The method of claim 5 wherein aspirating the guide catheter includes actuating a syringe.

7. The method of claim 1 wherein the funnel member is coupled to the distal portion of the guide catheter.

8. The method of claim 1 wherein advancing the clot treatment device through the lumen of the guide catheter includes advancing an elongated tubular structure having a distal portion coupled to the clot treatment device.

9. The method of claim 8 wherein expanding the clot treatment device includes expanding the clot treatment device in a direction radially away from the elongate tubular structure.

10. The method of claim 1 wherein expanding the funnel member includes expanding the funnel member to a diameter that is less than a diameter of the blood vessel.

11. The method of claim 1 wherein the proximally-facing curved portion defines a convex surface, and wherein the distally-facing curved portion defines a convex surface.

12. The method of claim 1 wherein the treatment portions include at least three treatment portions spaced apart from one another.

13. A method of treating clot material in a blood vessel, the method comprising:
    advancing a clot treatment device in a low-profile state through a lumen of a guide catheter, wherein the clot treatment device includes a mesh structure;
    at least partially expanding the clot treatment device within the blood vessel from the low-profile state to a deployed state, wherein, in the deployed state—
    the mesh structure includes at least three treatment portions spaced apart from one another,
    individual ones of the treatment portions include a proximally-facing curved portion and a distally-facing curved portion, and
    the proximally-facing curved portion and the distally-facing curved portion have the same radius of curvature;
    expanding a funnel member within the blood vessel proximal of the clot material and such that the funnel member has a diameter that is less than a diameter of the blood vessel;
    engaging the clot treatment device with the clot material;
    retracting the clot treatment device and a portion of the clot material into a distal portion of the guide catheter; and
    inhibiting, with the funnel member, the clot material from moving proximally through the blood vessel past the distal portion of the guide catheter during retraction of the clot treatment device and the portion of the clot material into the distal portion of the guide catheter.

14. The method of claim 13 wherein the method further comprises aspirating the lumen of the guide catheter with a syringe during retraction of the clot treatment device and the portion of the clot material into the distal portion of the guide catheter.

15. The method of claim 13 wherein advancing the clot treatment device through the lumen of the guide catheter includes advancing an elongated tubular structure having a distal portion coupled to the clot treatment device.

16. The method of claim 15 wherein expanding the clot treatment device includes expanding the clot treatment device in a direction radially away from the elongate tubular structure.

* * * * *